United States Patent [19]

Rotondo

[11] Patent Number: 4,942,165

[45] Date of Patent: Jul. 17, 1990

[54] TREATMENT FOR ALZHEIMER'S DISEASE

[75] Inventor: Richard D. Rotondo, St. Paul, Minn.

[73] Assignee: Advanced Biologics, Inc., Minneapolis, Minn.

[21] Appl. No.: 276,818

[22] Filed: Nov. 28, 1988

Related U.S. Application Data

[63] Continuation of Ser. No. 828,763, Feb. 11, 1986, Pat. No. 4,814,339.

[51] Int. Cl.$^5$ ...................... A61K 31/44; A61K 31/52
[52] U.S. Cl. ...................... 514/261; 514/332
[58] Field of Search ...................... 514/332, 261

[56] References Cited

U.S. PATENT DOCUMENTS

| | | | |
|---|---|---|---|
| 3,016,378 | 1/1962 | Roch | 424/266 |
| 3,651,045 | 3/1972 | Haskell et al. | 424/253 |
| 3,825,541 | 7/1974 | Vince | 424/253 |
| 3,920,823 | 11/1975 | Meyer et al. | 424/253 |
| 4,011,329 | 3/1977 | Fake | 424/253 |
| 4,048,432 | 9/1977 | Baker | 424/253 |
| 4,055,717 | 10/1977 | Baker et al. | 424/253 |
| 4,055,718 | 10/1977 | Baker | 424/253 |
| 4,138,562 | 2/1979 | Vince | 424/253 |
| 4,268,672 | 5/1981 | Vince | 424/253 |
| 4,271,170 | 6/1981 | Tanouchi et al. | 424/262 |
| 4,317,828 | 3/1982 | Tanouchi et al. | 424/262 |
| 4,321,376 | 3/1982 | Otani et al. | 424/262 |
| 4,338,310 | 7/1982 | Vince | 424/262 |
| 4,362,729 | 12/1982 | Vince | 424/262 |
| 4,370,334 | 1/1983 | Sato | 424/262 |
| 4,383,114 | 5/1983 | Vince | 424/262 |
| 4,450,165 | 5/1984 | Araki et al. | 424/262 |
| 4,624,852 | 11/1986 | Wurtman | 424/262 |
| 4,624,946 | 11/1986 | Scolastico et al. | 424/262 |
| 4,742,064 | 5/1988 | Vince | 424/262 |

OTHER PUBLICATIONS

"Effects of Δ9-Tetrahydrocannabinol on Regional Brain Acetylcholine", Univ. of Mich., pp. 673-678, Domino et al.
Chemical Abstracts, vol. 88, 6668n, 1978.
Chemical Abstracts, vol. 89, 41983d, 1978.
"Intrahippocampal Septal Grafts . . . in Aged Rats", Science, Aug. 3, 1984, vol. 225, pp. 533-535, Gage et al.
"Alzheimer's Disease . . . Formation", Science, Sep. 14, 1984, vol. 225, pp. 1168-1170, Hyman et al.
"Neuronal Phosphoproteins . . . Implications", Science, Sep. 21, 1984, vol. 225, pp. 1357-1364, Nestler et al.
"Turnover of Inositol Phospholipids and Signal Transduction", Science, Sep. 21, 1984, vol. 225, pp. 1365-1370, Nishizuka.
"Effects of Dietary Choline on . . . Brain", Ohio State Univ., pp. 237-245, Pendley II et al., 1985.
"Are the Phospholipids . . . Synthesis?", Boston Univ. School of Medicine, pp. 229-235, Blusztajn et al., 1985.
"Phospholipase Activities in Rat Brain Areas During Aging", Universita di Perugia, pp. 151-161, Gaiti et al., 1985.
"Metabolic and Functional Aspects of . . . Phospholipids", Ohio State Univ., pp. 341-343, Farooqui et al., 1985.
"Evaluation of the Brain-Specific Delivery . . . Carrier", J. Med. Chem. 1985, pp. 1574-1580, Tedjmulia et al.
"Phosphatidylinositol . . . Handling of Myo-Inositol", Chil. Hosp. of Phil., pp. 1073-1080, Berry et al., 1986.
"Phospholipids as Pharmacological Tools in the Aging Brain", Fidia Research Lab., pp. 11-17, Calderini et al., 1985.
"Advancing Frontiers in Alzheimer's Disease Research," ed. by G. Glenner and R. Wurtman, Univ. of Texas, pp. 1-9, 1987.

Primary Examiner—Stanley J. Friedman
Attorney, Agent, or Firm—Burd, Bartz & Gutenkauf

[57] ABSTRACT

Hydropyridine analogs, dihydropyridine analogs, trihydropyridine analogs, hydropurine analogs, dihydropurine analogs, trihydropurine analogs, N,N,N,'-trimethyl- N'-(2-hydroxy-3-methyl-1,3-propanediamone analogs, 1-methyl-3-[N-(4-iodophenyl)- carbamoyl]-1,4-dihydropyridine analogs, that are lipid-soluble with the specific electron charge density and therefore useful for the administration of several compounds that need to penetrate the blood-brain capillary barrier. Once inside the brain these compounds undergo NAD-NADH reduction thereby providing for a brain serum retention. These compounds having been modified herein to deliver various compounds, some of which are those that are progressively absent during the course of a disease called Alzheimer's Disease.

15 Claims, No Drawings

TREATMENT FOR ALZHEIMER'S DISEASE

This a continuation of application Ser. No. 828,763 filed Feb. 11, 1986, now U.S. Pat. No. 4,814,339.

BACKGROUND OF THE INVENTION

I have found that the deterioration of specific regions of the brain that is commonly called Alzheimer's Disease, is a factor of the result of the reduction in the levels of acetylcholine being produced. Due to the physiological changes beginning with the reduction of the tidal oxygen supply, the metabolic pathways that produce acetylcholine are disrupted. This, along with the reduction of brain activity is indicated by the reduction of the homo-oxygen utilization. In addition the utilization of Glycogen—(Glucose) metabolics are disrupted. Therefore the bonding of Actylcholine and these other compounds with suitable transport compounds discribed herein to produce an effective regulating means by which the degeneration, associated with Alzheimer's Disease, seen as neurofibrillatory tangles can be halted.

The hypoxia breakdown of cell membrane functions can be best illustrated by considering the human brain, one of the most hypoxia-sensitive organs in the mammalian body, for which events during various kinds of energy perturbations are well defined. In complete cerebral ischemia, the electroencephalograph (EEG) becomes isoelectric within 15 to 20 seconds. This electrically silent period precedes a massive outflux of K+ from the neurons and a flux of Na+ into the neurons, attributable to energy insufficiency and thus to the failure of membrane ion pumps, (at regional cerebral blood flow of about 10 percent of normal). When the potassium concentration (K+) in the extracellular fluid (ECF) drops to about 12 to 13 mM, changes in membrane potential apparently become large enough to activate voltage-dependent Ca+ channels and develop a largely uncontrollable influx of Ca+ a cation which at abnormally high cytosolic concentration acts as a cellular toxin.

Although high cytosolic cations (Ca2+) are what disrupt various intercellular functions, its activations of phospholipases A1, A2 and C, are considered to be the most damaging under hypoxic conditions to the cell membrane. Therefore increasing the brain serum concentrations of lysophosphatidylcholine, (lysoPC) and the other free fatty acids soon after ischemia are indicative of catalysis by phospholipases of the A class. For phospholigase A2, this catalysis can become cytotoxic. Uncontrolled, this reaction leads to membrane phospholipid hydrolysis, to the release of fatty acids (such as arachidonic acid), and to the further potentiation of ion redistributions. Therefore since long chain fatty acids have only a limited ability to cross the inner membrane as CoA thioesters, their entry is greatly stimulated by carnitine acyltransferase, which catalyzes transfer of the fatty acyl group from its thioester linkage with CoA to an oxygen-ester linkage with the hydroxyl group of carnitine. Since the standard-free energy change of this reaction is quite small, the acyl carnitine linkage represents a high energy bond. The O-acyl carnitine ester so formed then passes through the inner membrane into the matrix, via this specific transport system.

In the last stage of the entry process the acyl group is transferred from carnitine to intramitochondrial CoA by the action of a second type of carnitine acyltransferase located on the inner surface of the inner membrane. This complex entry system has the effect of keeping the extramitochondrial and intramitochondial pools of CoA and fatty acids separated. The intramitochondrial fatty acyl-CoA now becomes the substrate of the fatty acid oxidation system, which is situated in the inner matrix compartment.

Therefore the overall impact of Glycogen limitation to the brain as summarized herein is similar in other tissues as well, although it may not be as rapid or extensive in more hypoxia-tolerant tissues. In myocardial ischemia, for example engery difficiencies and membrane failures are indicated by intracellular and extracellular changes in (Na+) and (K+), as well by a large influx of Ca2+, a loss of sarcolemmal Ca+, and a disruption of mitochondrial Ca2+ homeostasis. Analogous membrane failure with associated translocation of Ca2+ and other ions between intracellular and extracellular pools is found in the liver under Oxygen-limiting conditions and in acute renal failure in mammals and can be observed to occur generally in hypoxia-sensitive mammalian organs and tissues during a massive reduction of oxygen.

Such ion-flux-initiated, self-reinforcing cascades also can be facilitated by the action of phospholipase C, whose continued catalytic function under oxygen limiting conditions is indicated by increasing levels of stearoyl and arachidonoyl diacylglycerols coincident with decreasing levels of phosphatidylinositol (PI). The diacylglycerols are the main inhibitors during the secondary metabolic process under which acetylcholine is being produced. Since the metabolic process for diacylglycerol reduces the availability of acyl-ions, the metabolic process for acetylcholine is then found lacking.

Also the major metabolic pathways responsible for the formation and degradation of (PI) are illustrated herein. Phosphatidylinositol is phosphorylated at the 4-position of its inositol head group by a specific kinase to form phosphatidylinositol 4-phosphate, [PII(4)P]; this is in turn further phosphorylated at the 5-position to give PI(4,5)P2, which is one of the inositol lipids located in the inner leaflet of the plasma membrane. The steady-state concentration of PI(4,5)P2 is determined by the balance between the activities of these kinases and phosphomonesterases, which convert PI(4,5)P2 back to (PI), that is, by the operation of two linked metabolic cycles in which phosphates are constantly being added to and removed from the 4 and 5 positions of the inositol head group.

In response to various Ca2+-mobilizing hormones, these two metabolic cycles are broken in a controlled way by preferential phospholipase C action on PI(4,5) P2, releasing diacylglycerol plus water-soluble inositol triphosphate (IP3) as a second messenger that signals release of Ca2+ from intracellular pools. In severe or prolonged hypoxia, in contrast, these cycles are broken in an apparently uncontrolled way, leading to the same end products. Inositol triphosphate released in the process as a secondary signal for opening Ca+ channels and releasing sarcoplasmic Ca+, increases cytosolic Ca2+ availability, a cascade that again is self-potentiating (increasing Ca2+ availability favoring phospholipase C catalysis). Under normal circumstances, diacylglycerol is phosphorlated to phosphatidic acid which is then converted back to PI.

However, diacylglycerol accumulates in hypoxia-sensitive tissues during diminished oxygen levels and can increase Na+-H+, exchange, thus effectively slowing down Na+ exchange-based Ca2+ efflux, which in turn inhibits the synthesis of acetylcholine, (ACh) by reducing the influx of choline and diverting the availability of acyl ions.

In hypoxia-sensitive tissues, as soon as continuous and high rates of ATP generation are reduced, intracellular and extracellular ion concentration gradients are rapidly lost and neuronal tissue viability is at risk In contrast, ionic concentration gradients do not fall to their thermodynamic equilibrium in homologous tissues of ectothermic anaerobes during hypoxia, being that they have mechanisms that can proctect them, to a greater degree than human beings.

In addition, 7-phosphonoheptanoic acid being an N-Methyl-D-Aspartate, (NMDA) Antagonist. It has been shown that 7-phosphonoheptanoic acid, (7AP) can reduce the damage by as much as 90% during reversible, insulin-induced, hypoglycemic coma. Neuronal necrosis due to hypoglycemic conditions is induced by agonists acting on the N-methyl-D-aspartate (NMDA) receptors in the caudate nucleau, one of the first areas affected by Alzheimer's Disease.

Therefore hypoglycemic brain damage is mediated by excitotoxins. First, at the onset of isoelectric EEG, the extracellular levels of aspartate and glutamate are markedly increased. Second, unilateral ablation of the motor cortex, transecting the corticostriatal projections and decreasing the ipsilateral striatal content of glutamate by ten percent, protects the subjacent caudate nucleus against neuronal necrosis after 30 minutes of hypoglycemic coma. This indicates that synaptic events are important for the induction of this secondary neuronal necrosis. Futhermore, in view of an electron microscope investigation, the dentate gyrus granule cell which is vulnerable to severe hypoglycemia as revealed in a dendro-somatic, axon-sparing lesion, that is similar to the ultrastructural characteristics as observed in the secondary excitotoxin-induced neuronal damage, which due to the limited supply of oxygen is not a major factor in the progression of the Alzheimer's Disease.

As in severe hypoglycemia, cerebral ischemia leads to extenstive engery deprivation, membrane depolarization, and an increase in extracellular levels of excitatory amino acids, since AP7 ameliorates the acute morphological changes in the hippocampus induced by ischemia.

Similar pathogenic mechanisms do prevail in the two disorders. However, the distribution of neuronal necrosis after ischemia is different from that after hypoglycemia. This that the NMDA receptor agonists released from their origin, and their regional extracellular concentrations are related.

In experiments with the uptake of choline into synaptosomes under high affinity conditions (0.5 micro molar choline) the transport of choline depends on the presence of Na+ ions. When Na+ ions are replaced with Li+ or sucrose, the rate of the high affinity uptake is diminished by 97% or 95% respectively; low affinity is lowered by 61% or 46% respectively. The choline influx in accordance with its own electrochemical gradient operates without an expenditure of energy transport Na+. Ca2+ in a co-, transportation across the neuro-membrane, is dependent upon the concentrations of choline. Ca2+ and Mg2+ can support the influx of choline better than Na+, which is different from the influx of glucose or other amino acids into the presymatic neurons. Optimum concentration of K+ ions in the range of 0.35-4.8 mM reduces the uptake by almost 50% and more than 90% in the presence of 62 mM K+. These results indicate that the reduction of the high affinity by K+ induced depolarization due to the membrane depolarization, is the driving force of choline uptake. This can also be supported by the fact that the absence of Ca2+ ions increases in a near linear progression the efflux of choline from neurons and glia in culture. The effects of metabolic inhibitors change the resting membrane potential. The availability of the compounds used for metabolic transformations of choline in the cells (ATP, acetyl-CoA), is affected by ionophores in accord with changes in transmembrane electric potentials. Therefore the high affinity transport of choline is closely associated with the synthesis of acetylcholine and therefore with cholinergic neurons. This is supported by the similarities between the regional distribution of the high affinity transport and ChAT parallel changes of the high affinity transport and ChAT during ontogeny and after lesions of the neural tracts. This is also supported by the process of stimulating the high affinity transport by evoking the release of ACh, the high degree to which the choline that is transported by the high-affinity mechanism is then converted to ACh, the inhibition of the synthesis of ACh by factors inhibiting the high affinity carrier (hemicholinium-3, lack of Na+) and by our many other laboratory observations. Evidence has been obtained indicating that, within the cholinergic neurons, the high-affinity carriers are localized in the nerve terminals (where the synthesis of ACh mainly occurs), whereas the membrane of neuronal perikara is equipped with the low affinity carriers. The rates of the influx and efflux of choline into and from the erythrocytes and synaptosomes depend on the concentration of choline on the opposite side of the membrane. The rate of transport in either direction can be increased by increasing (within limits) the concentration of choline in the compartment into which it is transported. In the synaptosomes the maximal influx and efflux were equal at saturating concentrations of choline in the trans position. The carrier mediates transport in both directions and its binding site translocates faster when it is loaded with choline or a related compound than when it is unloaded. The increase in the efflux of labelled choline from brain cell cultures occurring when the cells are exposed to a higher concentration of choline in the medium represents an example of the trans-activation of choline efflux. The uptake of choline into presynaptic nerve endings is enhanced by increased impulse activity or by conditions simulating it such as high K+ or veratridine. The uptake of choline is dependent on the presence of Ca2+ ions in transmitter release. Therefore the depolarization-induced stimulation of choline uptake is a consequence of ACh release during preincubation. The choline used for the synthesis of ACh in the nerve terminals mainly originates from the pool of free choline in the extracellular fluid surrounding the terminals. Choline is supplied to the sites of synthesis by carriers in the terminal membranes. The brain choline in the extracellular fluid is derived from phospholipids and glycerylphosphorylcholine in neurons and glia from choline in the blood and from ACh, released by nerve impulses and hydrolysed in synaptic clefts, are present in quantities such that the loss of acyl ions is the problem during the metabolic process of ACh formation. Therefore the transportation of choline into the presymatic neurons involves a close association in specific locations of the carrier for choline with enzymes metabolizing choline, like ChAT and or choline kinase, in addition to the specific transport quantities found in the presymatic neuron cell membrane.

SUMMARY OF THE INVENTION

The invention is directed to the lipophilic brain specific choline delivery compounds which include but are not limited to compounds that are useful in the treatment of a degenerative process known as Alzheimer's Disease. The compound are based on a pyridinium-dihydropyridine, and, or a purine-dihydropurine redox carrier(s). This redox delivery system is effected by a quaternary precursor which while retained within the brain can provide for a substained release of the specific compound(s) bonded to the carrier(s). The CO-NH bond is then cleaved enzymatically which thereby regenerates the original impermeable form thereby trapping the compounds within the brain. The transporting compounds are derived from pyridine, purine, N,N,N'-trimethyl-N'-(2-hydroxy-3-methyl)-1,3-propanediamine, dihydromethyl-glucose 6-phosphonenolpyruvate bases, and the like. Examples of carrier compounds bonded to acetylcholine are as follows: N,N,N'-trimethyl-N'-[2-hydroxy-3-methylacetylcholine]-1,3-propanediamine; hydropyridine-acetylcholine; dihydropyridine-acetylcholine; trihydropyridine-acetylcholine; hydropurine-acetylcholine; dihydropyridine-methyl-acetylcholine; trihydropyridine-methyl-acetylcholine; dihydrocarboxypyridine-acetylcholine; trihydromethylcarboxylpyridine-acetylcholine; dihydromethyl-glucose 6-phosphonenol-pyruvate-acetylcholine; trimethylacetyl-phosphate-dihydropyridine-acetylcholine; dihydropyridine-N-carboxybiotinyllysine-pyridoxal-phosphate-triacetylcholine; and 1-methyl-3-[N-(4-iodophenyl)-carbamoyl]-1,4-dihydropyridine-acetylcholine.

I hereby claim the following:

1. A method of treatment of degenerative mental process in a living subject which consists of administering to said living subject in need of treatment an effective amount of a carrier compound bonded to acetylcholine for transporting choline to the brain, said carrier compound is hydropyridine.

2. A method of treatment of degenerative mental process in a living subject which consists of administering to said living subject in need of treatment an effective amount of a carrier compound bonded to acetylcholine for transporting choline to the brain, said carrier compound is dihydropyridine.

3. A method of treatment of degenerative mental process in a living subject which consists of administering to said living subject in need of treatment an effective amount of a carrier compound bonded to acetylcholine for transporting choline to the brain, said carrier compound is trihydropyridine.

4. A method of treatment of degenerative mental process in a living subject which consists of administering to said living subject in need of treatment an effective amount of a carrier compound bonded to acetylcholine for transporting choline to the brain, said carrier compound is dihydromethylpyridine.

5. A method of treatment of degenerative mental process in a living subject which consists of administering to said living subject in need of treatment an effective amount of a carrier compound bonded to acetylcholine for transporting choline to the brain, said carrier compound is trihydromethylpyridine.

6. A method of treatment of degenerative mental process in a living subject which consists of administering to said living subject in need of treatment an effective amount of a carrier compound bonded to acetylcholine for transporting choline to the brain, said carrier compound is dihydrocarboxypyridine.

7. A method of treatment of degenerative mental process in a living subject which consists of administering to said living subject in need of treatment an effective amount of a carrier compound bonded to acetylcholine for transporting choline to the brain, said carrier compound is trihydromethylcarboxypyridine.

8. A method of treatment of degenerative mental process in a living subject which consists of administering to said living subject in need of treatment an effective amount of a carrier compound bonded to acetylcholine for transporting choline to the brain, said carrier compound is trimethylacetylphosphatedihydropyridine.

9. A method of treatment of degenerative mental process in a living subject which consists of administering to said living subject in need of treatment an effective amount of a carrier compound bonded to acetylcholine for transporting choline to the brain, said carrier compound is dihydropyridine-N-carboxybiotinyllysinepyridoxalphosphate.

10. A method of treatment of degenerative mental process in a living subject which consists of administering to said living subject in need of treatment an effective amount of a carrier compound bonded to acetylcholine for transporting choline to the brain, said carrier compound is 1-methyl-3-[N-(4-iodophenyl)carbamoyl]-1,4-dihydropyridine.

11. A method of treatment of degenerative mental process in a living subject which consists of administering to said living subject in need of treatment an effective amount of a carrier compound bonded to acetylcholine for transporting choline to the brain, said compound is hydropurine.

12. A method of treatment of degenerative mental process in a living subject which consists of administering to said living subject in need of treatment an effective amount of a carrier compound bonded to acetylcholine for transporting choline to the brain, said compound is dihydropurine.

13. A method of treatment of degenerative mental process in a living subject which consists of administering to said living subject in need of treatment an effective amount of a carrier compound bonded to acetylcholine for transporting choline to the brain, said compound is trihydropurine.

14. A method of treatment of degenerative mental process in a living subject which consists of administering to said living subject in need of treatment an effective amount of a carrier compound bonded to acetylcholine for transporting choline to the brain, said carrier compound being derived from a N,N,N'-trimethyl-N'-(2-hydroxy-3-methyl)-1,3-propanediamine.

15. A method of treatment of degenerative mental process in a living subject which consists of administering to said living subject in need of treatment an effective amount of a carrier compound bonded to acetylcholine for transporting choline to the brain, said carrier compound being derived from a dihydromethylglucose 6-phosphonenol-pyruvate.

* * * * *